(12) United States Patent
Mincu

(10) Patent No.: US 7,859,671 B2
(45) Date of Patent: Dec. 28, 2010

(54) METHOD FOR DETERMINING OPTICAL PROPERTIES OF TURBID MEDIA

(75) Inventor: Niculae Mincu, Dorval (CA)

(73) Assignee: ART, Advanced Research Technologies Inc., St. Laurent, QC (CA)

( * ) Notice: Subject to any disclaimer, the term of this patent is extended or adjusted under 35 U.S.C. 154(b) by 416 days.

(21) Appl. No.: 11/813,124

(22) PCT Filed: Dec. 22, 2005

(86) PCT No.: PCT/IB2005/003870

§ 371 (c)(1),
(2), (4) Date: May 5, 2008

(87) PCT Pub. No.: WO2006/070252

PCT Pub. Date: Jul. 6, 2006

(65) Prior Publication Data

US 2009/0103096 A1    Apr. 23, 2009

Related U.S. Application Data

(60) Provisional application No. 60/640,045, filed on Dec. 30, 2004.

(51) Int. Cl.
*G01N 21/00*    (2006.01)
*G01N 21/64*    (2006.01)
*A61B 5/00*    (2006.01)

(52) U.S. Cl. .................. 356/432; 250/458.1; 600/448; 600/332; 600/476

(58) Field of Classification Search ......... 356/432–444, 356/317, 318; 250/458.1–461.2; 600/448, 600/407, 332, 473, 476
See application file for complete search history.

(56) References Cited

U.S. PATENT DOCUMENTS

| | | | | |
|---|---|---|---|---|
| 4,805,623 | A * | 2/1989 | Jobsis | 600/328 |
| 6,104,946 | A * | 8/2000 | Tsuchiya et al. | 600/476 |
| 6,640,116 | B2 * | 10/2003 | Diab | 600/322 |
| 6,954,663 | B2 * | 10/2005 | Hall | 600/322 |
| 6,992,762 | B2 * | 1/2006 | Long et al. | 356/317 |
| 7,047,057 | B2 * | 5/2006 | Hall et al. | 600/407 |
| 7,446,875 | B2 * | 11/2008 | Wake et al. | 356/432 |
| 2004/0181153 | A1 * | 9/2004 | Hall | 600/448 |
| 2005/0107694 | A1 * | 5/2005 | Jansen et al. | 600/431 |
| 2006/0058685 | A1 * | 3/2006 | Fomitchov et al. | 600/476 |
| 2007/0158585 | A1 * | 7/2007 | Hall et al. | 250/458.1 |

* cited by examiner

*Primary Examiner*—Sang Nguyen
(74) *Attorney, Agent, or Firm*—BCF LLP

(57) ABSTRACT

There is provided a method for improving contrast and resolution of an optical image of an object obtained by time-resolved techniques such as Time Domain (TD) and Frequency Domain (FD). The method comprises obtaining a Temporal Point Spread Function (TPSF), and determining optical properties of volumes of interest (VOI), each volume being defined by an ensemble of equiprobable effective photon paths corresponding to a time point or time gate of the TPSF.

15 Claims, 2 Drawing Sheets

US 7,859,671 B2

METHOD FOR DETERMINING OPTICAL PROPERTIES OF TURBID MEDIA

CROSS-REFERENCE TO RELATED APPLICATIONS

This is the first application filed for the present invention.

TECHNICAL FIELD

This invention relates to the determination of optical properties in turbid media.

BACKGROUND OF THE INVENTION

Optical imaging is a promising alternative to imaging modalities such as X-rays, MRI, ultrasound, PET and the like and possesses advantages such as using non-ionizing radiation and being able to provide functional in addition to anatomical information.

It is well known from classical models, diffusion and transport equations and experimental measurements that time resolved methods such as Time Domain (TD) and Frequency Domain (FD) optical imaging can be exploited to recover optical properties of the medium by forward or inverse problems modeling (Hawrysz and Sevick-Muraca Neoplasia, Vol. 2 No. 5 pp 388-417, 2000). However, these calculations are time consuming and very sensitive to noise due to the number of free parameters required. These limitations are particularly felt in optical imaging.

Furthermore, the aforementioned calculations often assume that the volume sampled is homogeneous with regard to the optical properties of the underlying medium. This, of course, greatly reduces the spatial resolution of the determination of optical properties.

More direct approaches have been suggested to determine optical properties of turbid media using time domain. For example U.S. Pat. No. 5,386,827 describes a TD method to determine the absorption coefficient of a biological tissue based on the decay slope of the TPSF. However, this approach does not solve the problem of spatial resolution in the case where the medium is inhomogeneous with respect to its optical properties.

There is therefore a need for improved methods for determining the spatial distribution of optical properties in heterogeneous media.

SUMMARY OF THE INVENTION

In one aspect of the present invention there is provided a method for determining the optical properties of an heterogeneous medium with increased spatial resolution. The method comprises obtaining a Temporal Point Spread Function (TPSF), and determining optical properties of volumes of interest (VOI), each volume being defined by an ensemble of equiprobable effective photon paths corresponding to a time point or time gate of the TPSF. The method therefore advantageously provides for the determination of optical properties within volumes that are smaller than the sum of the volumes comprising all possible photon paths that give rise to the complete TPSF thereby increasing the spatial resolution. These smaller volumes can be defined by ellipsoids comprising the effective photon paths associated with corresponding time gates of the TPSF.

In an embodiment the absorption coefficient of the medium in a particular ellipsoid is determined using characteristics of the TPSF and a light transmission equation such as the Beer-Lambert equation applied to a particular time point or time gate intensity of the TPSF.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION OF THE PREFERRED EMBODIMENT

While the following detailed description will emphasize Time Domain (TD) examples, it will be appreciated that the invention may also apply to the Frequency Domain (FD) modality. The two approaches are generally referred to as time resolved and are related to each other by the Fourier Transform (FT).

Temporal Point Spread Functions (TPSF) provide an intensity profile of photons reaching a detector as a function of time. A TPSF can be acquired by measuring the intensity of an optical signal emanating from an object after a brief pulse of light has been introduced in the object. Alternatively, it can be obtained, in the FD, by Fourier transforming a harmonic signal obtained by introducing an amplitude modulated light source at a plurality of frequencies. Details relating to apparatus and method for acquiring TD and FD optical data are well known in the art.

The time at which a photon reaches the detector is correlated to its effective path within the medium. Thus, all photons reaching the detector at the same time have the same effective path. In one aspect of the present invention, optical absorption coefficients of volumes of interest (VOI's), defined by the envelope of equiprobable photon paths giving rise to the signal at a predetermined time point or time gate of a temporal point spread function (TPSF), are obtained.

Photon migration theory predicts that the detected photons paths can be represented by a three dimensional ellipsoid ("cigar-shaped") distribution pattern in the transmission mode or by a "semi" ellipsoid ("banana-shaped") distribution in the reflection mode. Various techniques such as Monte Carlo simulations have provided support for the existence of the ellipsoid-shaped paths distributions.

Figure 1:
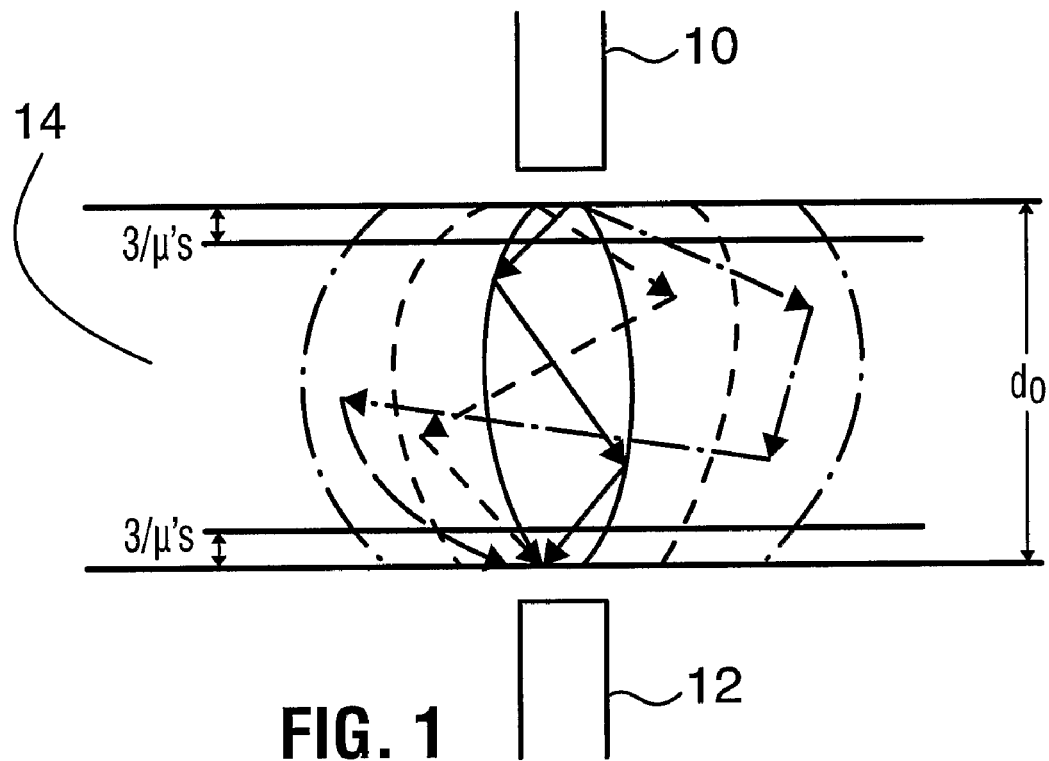
FIG. 1 is a schematic representation of a source-detector in the transmission configuration and the associated ellipsoids.

FIG. 1 schematically represents an embodiment of the present invention in which a TPSF is obtained in the transmission mode, that is to say, light is injected on one side of an object and detected on the opposite side (also referred to as co-axial configuration in which the source and detector are located substantially along the same axis). The photons arriving at the detector at a given moment correspond to photons having traveled a given effective path. By effective path it is meant the total path length traveled by a photon during the propagation through a diffusing medium between the source point and detection point. Thus, for a given time point of the TPSF, the signal will result from the contribution of all photons traveling different paths but all having substantially the same path length or effective path.

For example, the ellipsoid comprising the paths giving rise to $T_{max}$ is the ellipsoid comprising photon paths with the maximum probability of detection. The photons arriving before or after $T_{max}$ will travel a shorter or longer effective path respectively. As can be appreciated from FIG. 1, shorter effective paths are comprised within a smaller volume than longer effective paths. The parameters that defines the size and shape of the ellipsoid with maximum probability of detection are determined based on the following: A photon has a maximum probability of being detected if the path of this photon passes through a point at which the probability of redistribution through diffusion is uniform in all directions. This means that any photon which at one moment during its propagation is located in this "focal" point has a maximum probability of being detected independent of its initial direction of propagation. The position of this point is a function of the diffusion coefficient of the medium in which propagation takes place and is symmetric, with respect to the source-detector configuration, to the point at which the injected pulse is converted into an isotropic source. The position of this point is approximately $3/\mu_s'$ from the surface for a scattering coefficient $\mu_s' \sim 1/mm$ which is typical of biological tissues. This is based on the assumption that after traveling a distance equivalent to 3 times the reduced mean free path (mfp=$1/\mu_s'$) the photons are completely diffused. Thus the ellipsoid corresponding to the maximum of the TPSF can be characterized as follows: focal points are localized $3/\mu_s'$ from the surface, the long axis $d_0 = 2a$ where $d_o$ is the distance between the source 10 and the detector 12, which also corresponds to the sample 14 thickness and a has the usual meaning in ellipsoid geometry and the distance between the focal points is given by $$2c = 2a - 2*3/\mu_s' \quad (1)$$

The third parameter required for the complete determination of the ellipsoid is evaluated using the well known relation:

$$b = \sqrt{a^2 - c^2} \quad (2)$$

where b is equal to half of the short axis. Thus the ellipsoid corresponding to the maximum probability of detection can be defined by:

$$a = d_o/2 \quad (3)$$

$$b = 1/\mu_s' * \sqrt{3*(d_o * \mu_s' - 3)} \quad (4)$$

$$c = d_o/2 - 3/\mu_s' \quad (5)$$

The parameters of a generic ellipsoid corresponding to a longer effective path length (photons arriving at later times ($T_i$) than the ones corresponding to the maximum) can be obtained from the following relations:

$$a = (d_o/2) * T_i/T_{max} \quad (6)$$

-continued $$b = d_o/2 * \sqrt{(T_i/T_{max})^2 - \left(1 - \frac{6}{(d_o * \mu_s')}\right)^2} \quad (7)$$

$$c = d_o/2 - 3/\mu_s' \quad (8)$$

where $T_{max}$ is the time of arrival of the photons corresponding to the maximum of the TPSF.

Figure 3:
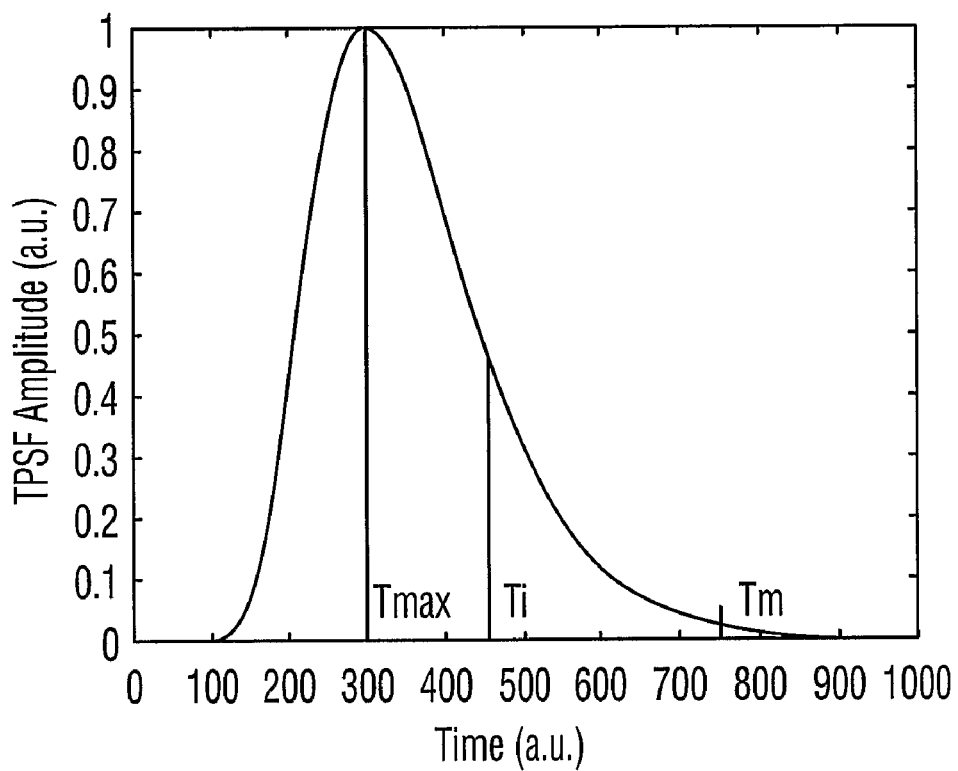
FIG. 3 is an example of TPSF sampling for determination of ellipsoids.
Figure 4:
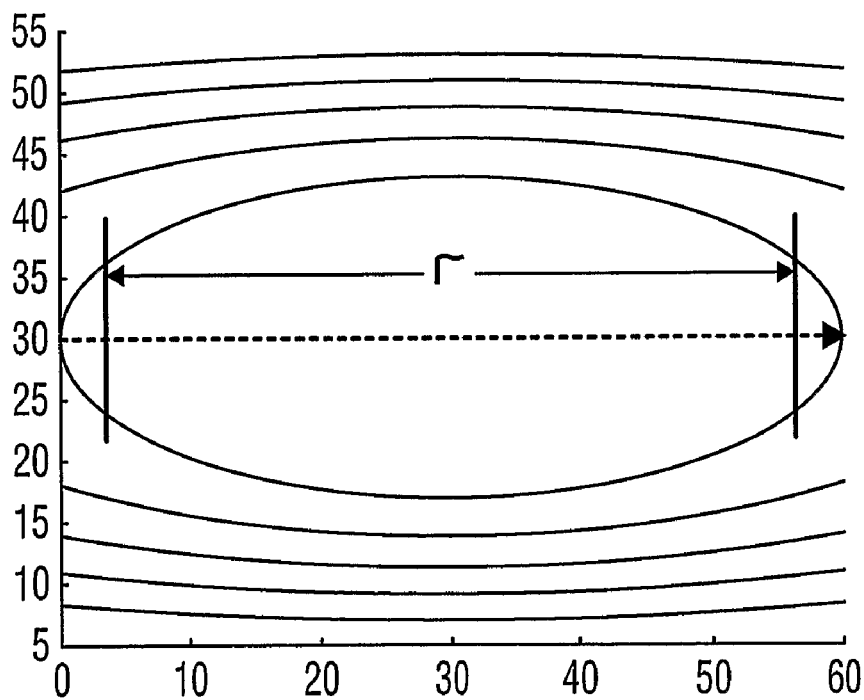
FIG. 4 is an example of ellipsoids obtained from TPSF sampling.

The VOIs can be determined by modeling the volume of the object with ellipsoids and correlating the ellipsoids with time points and/or time gates of the TPSF. Upon modeling, each source-detector configuration will generate a family of ellipsoids corresponding to the TPSF derived from measurements obtained with a particular source-detector configuration (see FIGS. 3 and 4).

The optical properties of the medium comprised within a given ellipsoid can then be estimated, thereby providing a map of an optical property for a volume of interest. To a good approximation the effective path is only dependent on the diffusion of the photons within the medium. That is to say, the time taken to reach the detector by a photon traveling the effective path is not influenced by absorption. Absorption only affects the intensity of the TPSF. Therefore, in one aspect of the invention, the TPSF can be used to estimate the absorption coefficient in a VOI using the intensity of the TPSF at a given time point as will be described below.

The most probable effective photon path corresponding to photons giving rise to the maximum intensity of the TPSF at $T_{max}$, can be calculated:

$$d_{eff}^{max} = d_o T_{max}/t_o = c*T_{max} \quad (9)$$

where $d_o$ is the geometrical thickness (source-detector distance in straight line); $t_o$ the time of propagation through the medium, from source to detector, in straight line; and c is the speed of light in the medium. Relation (9) can be generalized to all time points ($T_i$) of the TPSF:

$$d_{eff}^i = c*T_i \quad (10)$$

In one embodiment of the invention, a light transmission equation can be used to derive the absorption coefficient. For example, the Beer-Lambert law can be used to estimate the absorption coefficient in an ellipsoid. Thus, for a time point $T_i$ of the TPSF, and by considering equation 10, the corresponding amplitude of the signal can be written:

$$I_i = I_o \exp(-\mu_{a,i} * d_{eff}^i) = I_o \exp(-\mu_{a,i} * c * T_i) \quad (11)$$

Equation (11) is preferably applied to photons arriving after $T_{max}$ for which the amplitude of TPSF is mostly dependent on the absorption coefficient. For $T_i < T_{max}$ the amplitude of the TPSF still depends on the redistribution of the photons due to diffusion. It is possible to estimate the diffusion and subtract it from the intensity of the TPSF to yield an absorption measurement free of diffusion. The correction factor can be derived as follows for scattering coefficients in the range 8 $cm^{-1}$ to 15 $cm^{-1}$, typical of biological tissues, the pulse could be assumed as equivalent to an isotropic source after 2-3 mm from the surface. With the assumption that the source detector separation is large enough to maintain the validity of the diffusion theory, a correction factor could be derived from the dependence of the photon flux $\phi l$, for cw illumination:

$$\varphi I = \frac{1}{(4\pi Dr)\exp\left(-r\sqrt{(\mu_a/D)}\right)} \quad (12)$$

where $D=1/3\ \mu_s'$ is diffusion coefficient and r is the source-detector separation. Assuming $\mu_a$ is much smaller than $\mu_s'$, a good approximation for the typical tissue values, the decrease due to the scattering only is $S\sim 1/(4Dr)$ where D is the diffusion coefficient and r the distance from the source to the point where the measurement is performed. S is the correction factor for the decrease flux of the photons due to the scattering. For relative distribution only the dependence on r could be used. For absolute evaluations the diffusion coefficient need to be determined and for this a classical diffusion model in homogeneous media could be used (M. S. Patterson, B. Chance, B. C. Wilson, Applied Optics, (1989), 28:2331-2336; D Contini, F Martelli, and G Zaccanti. Applied Optics (1997); 36:4587-4599; incorporated herein by reference). For the reflection configuration some example of quantification is presented when this configuration is analyzed. For more details regarding the modeling of the homogeneous case see the above-cited references.

From equation 11 the value of the average absorption coefficient of the volume of the medium covered by the corresponding ellipsoid (corresponding to $T_i$) can be derived:

$$\mu_{a,i} = -1/(c^*T_i)^* \ln(I_i/I_o) \quad (13)$$

Thus, for each time point or time gate the average value of the absorption coefficient $\mu_{a,i}$ in the corresponding ellipsoid can be determined.

Evaluation of $I_o$ can be made directly from the source. However, in a preferred embodiment the following method can be used. For a time gate defined near the tail of the TPSF, $T_M$ we have:

$$\mu_{a,M} = -1/(c^*T_M)^* \ln(I_M/I_o) \quad (14)$$

The value of $\mu_{a,M}$ can also be derived using the asymptotic approximation as is well known from the prior art (M. S. Patterson, B. Chance, B. C. Wilson, Applied Optics, (1989), 28:2331-2336; D Contini, F Martelli, and G Zaccanti. Applied Optics (1997); 36:4587-4599; and U.S. Pat. No. 5,555,885, incorporated herein by reference), from the tail fitting of the TPSF:

$$\mu_{a,M} = K^*m(\ln(\text{TPSF}_{tail})) \quad (15)$$

where m is the symbol for the slope. From (5) and (6) we can derive the value for $I_o$:

$$I_o = I_M \exp(-c^*T_M^*K^*m(\ln(\text{TPSF}_{tail}))) \quad (16)$$

$T_M$ is the mean time corresponding to the points from the TPSF used in equation (15) to derive $\mu_{a,M}$. With the value for $I_o$ obtained from equation (16) one can evaluate the absorption coefficient for all ellipsoids corresponding to the time points $T_i > T_{max}$ of the TPSF by using equation (13).

In another aspect, the value of the average concentration of a chromophore $N_i$ for the corresponding ellipsoid of any time gate $T_i$ can also be evaluated:

$$N_i = -1/(c^*T_i^*\sigma)^* \ln(I_i/I_o) \quad (17)$$

$$N_i = -1/(c^*T_i^*\sigma)^* \ln(I_i/I_M \exp(-c^*T_M^*K^*m(\ln(\text{TPSF}_{tail})))) \quad (18)$$

where $\sigma$ is the extinction coefficient of the chromophore at a given wavelength.

If we assume that there are more than one chromophore in the medium, the concentration of each can be obtained by performing measurements for a number of wavelengths equal to the number of chromophores and developing a system of equations to solve for the concentrations as is well known in the art of multi-wavelength spectroscopic method. Relation (18) can be rewritten for each wavelength $\lambda$:

$$\Sigma N_j \sigma_j(\lambda) = -1/(c^*T_i(\lambda))^* \ln(I_i(\lambda)/(I_M(\lambda)^* \exp(c^*T_M(\lambda)^*K^*m(\ln(\text{TPSF}_{tail}(\lambda)))) \quad (19)$$

In yet another aspect of the invention, a local map of the relative absorption profile in the volume around the source-detector line can be drawn. For two successive time gates, $T_i < T_{i+1}$ the average values for the absorption coefficient are:

$$\mu_{a,i} = -1/(c^*T_i)^* \ln(I_i/I_o) \quad (20)$$

$$\mu_{a,i+1} = -1/(c^*T_{i+1})^* \ln(I_{i+1}/I_o) \quad (21)$$

If the values for $\mu_a$ are the same then the medium is homogeneous. If the values for $\mu_a$ are different the medium is heterogeneous and by differential evaluation a map of absorption coefficients can be generated. The differential value $\mu_a^d$ for the region outside the ellipsoid i but inside the ellipsoid i+1 can be evaluated from:

$$I_{i+1} = I_o \exp(-\mu_{a,i}^* d_{eff}^i)^* \exp(-\mu_a^{d*}(d_{eff}^{i+1} - d_{eff}^i)) = I_o \exp(-\mu_{a,i}^* c^* T_i)^* \exp(-\mu_a^{d*} c^*(T_{i+1} - T_i)) = I_i \exp(-\mu_a^{d*} c^*(T_{i+1} - T_i)) \quad (22)$$

$$\mu_a^d = -1/(c^*(T_{i+1} - T_i))^* \ln(I_{i+1}/I_i) \quad (23)$$

The absolute evaluation of the differential coefficient of absorption can also be obtained by beginning the iteration of equation (23) at time points near the tail of the TPSF for which we can evaluate the absorption coefficient using (15).

Assuming the absorption change is due to a change in concentration of one specific chromophore one can draw the profile of the concentration of that chromophore:

$$\mu_a^d = N^{d*} \sigma \quad (24)$$

Figure 2:
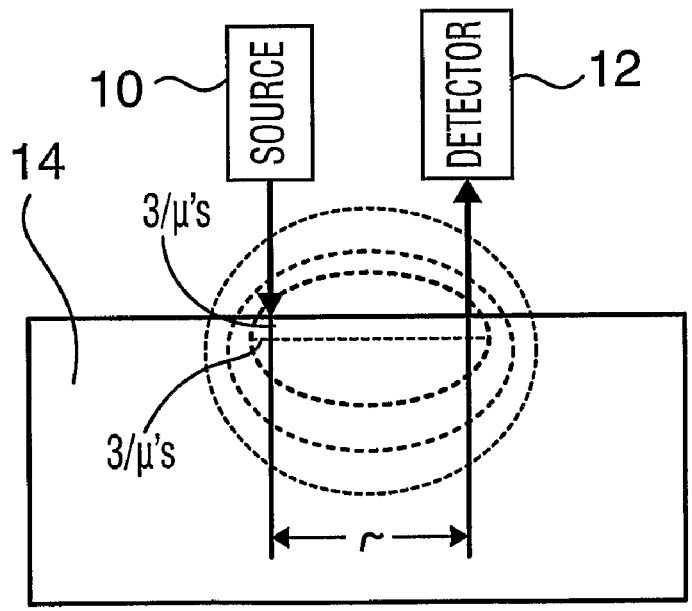
FIG. 2 is a schematic representation of a source-detector in the reflection configuration and the associated ellipsoids.

The relations described above can be applied to a reflection configuration (FIG. 2). The problem can be represented as in FIG. 2 where it can be seen that only "half" of the ellipsoid is within the medium. Even in the presence of the "boundary" generated by the presence of the surface, the equations derived for the transmission configuration can be used with an acceptable accuracy for the evaluation of the volume of the ellipsoid. In a preferred embodiment, the solution for asymptotic approximation of homogeneous media for determination of an absolute value of $\mu_a$ is used:

$$\ln[R(r,t)] = k - 5/2 * \ln(t) - (ct + 3r^2/(4ct))^* \mu_a - 3r^2/(4ct)^* \mu_s' \quad (25)$$

Where: $R(r,t)$ is the diffused reflectance and $k = -3/2 * \ln(4\pi cD) - \ln(\mu_a + \mu_s')$ The derivative $$\partial/\partial t (\ln[R(r,t)]) = -5/(2*t) - \mu_a^* c - r^2/(4*D^*c^*t^2) \quad (26)$$

reveals that for longer time the third term, which is linear in $\mu_a$, will have a determinant contribution. Therefore $\mu_a$ can be approximated from the asymptotic slope of the dependence of $\ln[R(r,t)]$ on time (M. S. Patterson, B. Chance, B. C. Wilson, Applied Optics, (1989), 28:2331-2336; and U.S. Pat. No. 5,555,885, incorporated herein by reference). From this relation is derived $\mu_{a,M}$ generically defined in equation (15).

In the reflection configuration (see FIG. 2), the ellipsoid corresponding to the maximum of the TPSF is defined by the following parameters:

$$2c = r \quad (27)$$

$$\text{and } 2a = r + 2*3/\mu_s' \quad (28)$$

The evaluation of a generic ellipsoid corresponding to $T_i$ can be done following the procedure previously described for transmission configuration.

It will be appreciated that the sensitivity to the presence of small inhomogeneities in the reflection configuration is greater due to the higher relative volume ratio (the volume of the ellipsoid is approximately half compared to transmission mode). In general, the reflection mode is more adequate for layered sample, with a profile of the absorption along the perpendicular to the surface.

In a further embodiment of the invention, quantitative evaluation of the concentration of an injected chromophore can be made by using measurements before and after the injection. We have for the same time gate $T_i$ an amplitude change from $I_b$ (before) to $I_a$ (after) and the corresponding change of $\mu_a$:

$$\mu_{a,b} = -1/(c*T_i)*\ln(I_b/I_o) \quad (29)$$

$$\mu_{a,a} = -1/(c*T_i)*\ln(I_a/I_o) \quad (30)$$

$$\mu_{a,a} - \mu_{a,b} = -1/(c*T_i)*\ln(I_a/I_b) \quad (31)$$

The increase of the absorption coefficient is due to the chromophore concentration N in the corresponding ellipsoid:

$$\mu_{a,a} - \mu_{a,b} = N*\sigma \quad (32)$$

where $\sigma$ is the cross section of the chromophore.

Combining the relations (15) and (16) one can evaluate the concentration:

$$N = -1/(c*T_i*\sigma)*\ln(I_a/I_b) \quad (33)$$

N is the average concentration of the chromophore in the volume of the ellipsoid corresponding to the time gate $T_i$. As will be appreciated, because equation (33) expresses a differential absorption measurement of the chromophore, the scatter contribution to the TPSF signal is eliminated and the earlier time points or time gates ($T_i < T_{max}$) can be used for absolute concentration evaluation with maximum spatial resolution and sensitivity.

From the above it can be appreciated that by determining $\mu_a$ for a plurality of ellipsoids corresponding to a plurality of time points or time gates of the TPSF maps of $\mu_a$ can be reconstructed. Furthermore, different spatial resolutions can be achieved by selecting early or late time points or time gates. In this respect it will be noted that for early time gates (small $T_i$) the spatial resolution of the absorption coefficient is greater since the corresponding ellipsoids comprise a smaller volume.

The spatial resolution may also be optimized by obtaining TPSF's from a plurality of source-detector configurations. It will be appreciated that family of ellipsoids may overlap. This overlapping may provide a further advantage in providing additional information about the optical properties of a given VOI. In particular, the reliability of optical properties determination in a VOI derived using ellipsoids corresponding to the tail end of the TPSF, which typically exhibits a lower signal to noise ratio, may be increased by scanning the same area using different source-detector configuration and therefore modeling the VOI with different ellipsoids. Alternatively, if the object is scanned in a raster fashion, the distances between the scan points can be adjusted so as to provide the desired resolution.

It will also be appreciated that the above described method can be used in a variety of applications. For example in optical imaging of biological tissues, is part of small animals or larger mammals such as humans, in which a map of the absorption coefficient could help to localize tumors and differentiate between tumors with different levels of activity in different regions of their volume due to the presence of different chromophores.

The method can also be useful for pharmacokinetics applications in which mapping of the concentration distribution of exogenous chromophores is often required.

The method can also be used as simple quantitative evaluation of the absorption and concentration of chromophores in any strongly diffusing solutions.

The embodiment(s) of the invention described above is(are) intended to be exemplary only. The scope of the invention is therefore intended to be limited solely by the scope of the appended claims.

The invention claimed is:

1. A method for determining an optical absorption coefficient of a volume of interest (VOI) in a turbid medium using time resolved optical modalities, said method comprising:
   injecting light in said medium at an injection point;
   detecting light exiting said medium at a detection point;
   generating a Temporal Point Spread Function (TPSF) using said detected light;
   correlating a predetermined time point or time gate of said TPSF with said VOI wherein said VOI comprises equiprobable effective photon paths; and
   determining said optical absorption coefficient within said VOI using one or more characteristics of said TPSF.

2. The method as claimed in claim 1 wherein said absorption coefficient is determined as a function of a light transmission equation incorporating said one or more characteristics of said TPSF.

3. The method as claimed in claim 2 wherein said light transmission equation is the Beer-Lambert equation.

4. The method as claimed in claim 3 wherein said step of determining said absorption coefficient comprises the step of estimating an intensity value for said injected light to calculate said absorption coefficient using said Beer-Lambert equation.

5. The method as claimed in claim 4 further comprising the step of determining a concentration of a chromophore using said intensity value and said Beer-Lambert equation.

6. The method as claimed in claim 5 wherein the concentration of two or more chromophores is determined by obtaining two or more TPSF's at two or more wavelengths.

7. The method as claimed in claim 3 wherein said Beer-Lambert equation is used for determining concentration of a chromophore by using the ratio of intensity of said TPSF at said time point or time gate for said VOI with and without said chromophore.

8. The method as claimed in claim 4 wherein said intensity value is determined as a function of the rate of decay of the asymptotic portion of said TPSF and a time point or time gate within said asymptotic portion.

9. The method as claimed in claim 1 wherein said determination of said absorption coefficient is a relative determination of two VOI's.

10. The method as claimed in claim in claim 1 wherein said TPSF is obtained in transmission mode.

11. The method as claimed in claim 1 wherein said TPSF is obtained in the reflection mode.

12. The method as claimed in claim 1 wherein said VOI is an ellipsoid.

13. The method as claimed in claim 1 wherein said time point or time gate is equal to or greater than time point corresponding to the maximum of said TPSF.

14. The method as claimed in claim 1 wherein said optical absorption coefficient is mapped for more than one VOI thereby producing an image of optical absorption coefficient of said medium in a region of interest (ROI).

15. The method as claimed in claim 14 wherein a plurality of TPSF's are obtained from a plurality of injection/detection points configurations to produce a plurality of images of said VOI and wherein said images are combined to produce an image of said VOI with enhanced resolution.

* * * * *